United States Patent [19]
Jacob et al.

[11] Patent Number: 5,893,856
[45] Date of Patent: Apr. 13, 1999

[54] APPARATUS AND METHOD FOR BINDING A FIRST LAYER OF MATERIAL TO A SECOND LAYER OF MATERIAL

[75] Inventors: Pamela A. Jacob, Foxboro; Edward F. Hoyle, Stoughton, both of Mass.

[73] Assignee: Mitek Surgical Products, Inc., Westwood, Mass., MA

[21] Appl. No.: 08/661,901

[22] Filed: Jun. 12, 1996

[51] Int. Cl.⁶ .................................................. A61B 17/08
[52] U.S. Cl. ........................ 606/151; 606/213; 606/219; 606/220; 411/446; 411/456
[58] Field of Search .................... 606/151, 213, 606/219, 220, 221, 64, 72, 75, 78; 411/446–450, 456–460

[56] References Cited

U.S. PATENT DOCUMENTS

| | | | |
|---|---|---|---|
| 285,295 | 2/1928 | Wells | 411/460 |
| 1,153,450 | 9/1915 | Schaff | 411/446 |
| 2,417,423 | 3/1947 | Lang | 411/458 |
| 4,655,659 | 4/1987 | Leemke | 411/359 |
| 4,736,560 | 4/1988 | Murphy | 52/410 |
| 5,002,562 | 3/1991 | Oberlander | 606/221 |
| 5,013,316 | 5/1991 | Goble et al. | 606/72 |
| 5,053,046 | 10/1991 | Janese | 606/213 |
| 5,217,486 | 6/1993 | Rice et al. | 606/232 |
| 5,234,447 | 8/1993 | Kaster et al. | 606/153 |
| 5,342,376 | 8/1994 | Ruff | 606/151 |
| 5,478,353 | 12/1995 | Yoon | 606/213 |
| 5,571,104 | 11/1996 | Li | 606/72 |
| 5,591,206 | 1/1997 | Moufarrege | 606/215 |

FOREIGN PATENT DOCUMENTS

285295   2/1928   United Kingdom ............ 411/460

*Primary Examiner*—Gary Jackson
*Assistant Examiner*—Tina T. D. Pham
*Attorney, Agent, or Firm*—Pandiscio & Pandiscio

[57] ABSTRACT

A fastener for binding a layer of mammalian soft tissue to a mammalian bone includes a body portion for disposition in a bore in the bone, the body portion having means thereon for resisting movement of the body portion from the bore. The fastener further includes gripper portions extending from the body portion and extendible through the layer of tissue toward the bone to bind the tissue to the bone. The invention further contemplates a method for making the fastener, a method for binding layers of material together using the fastener, a tool for setting the fastener, and tools and fasteners in combination.

2 Claims, 18 Drawing Sheets

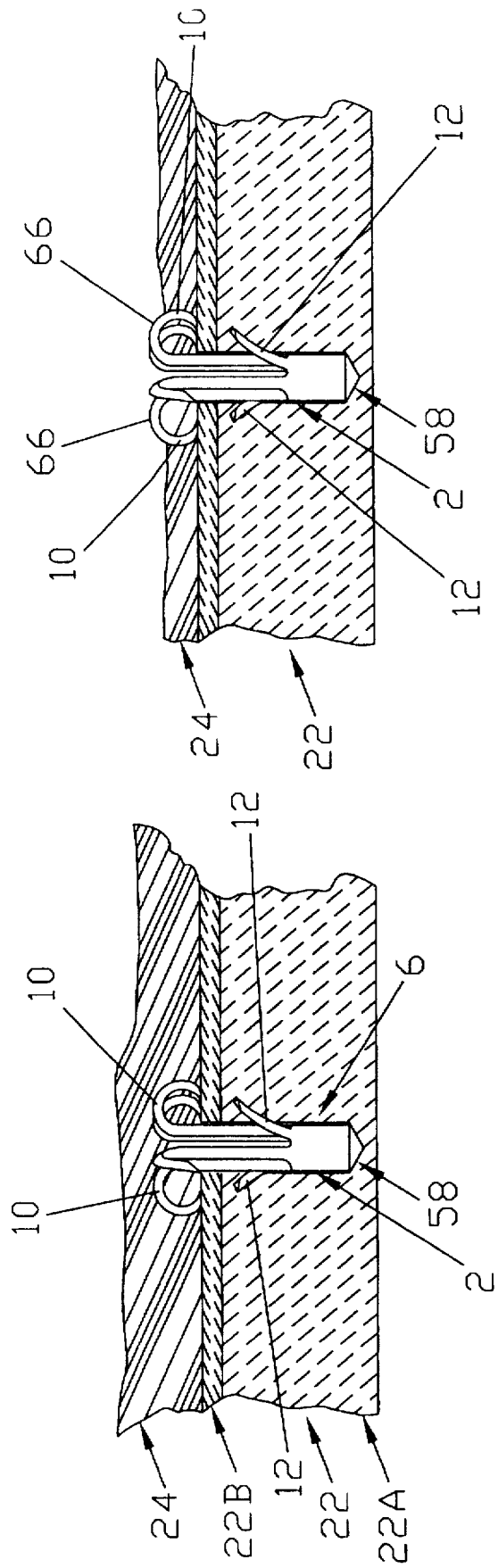

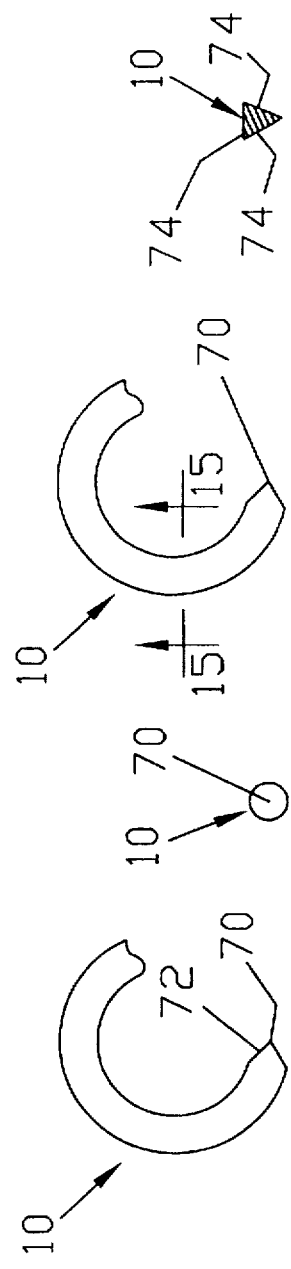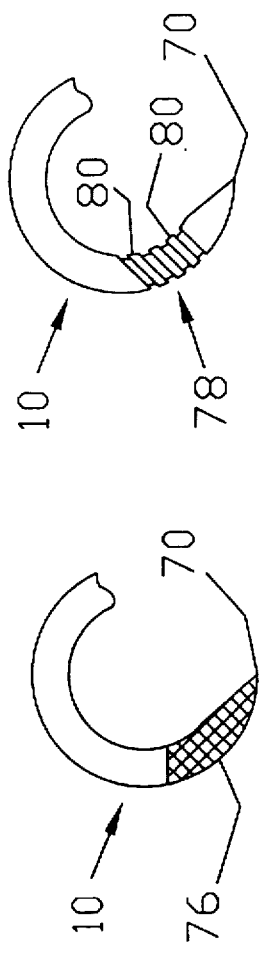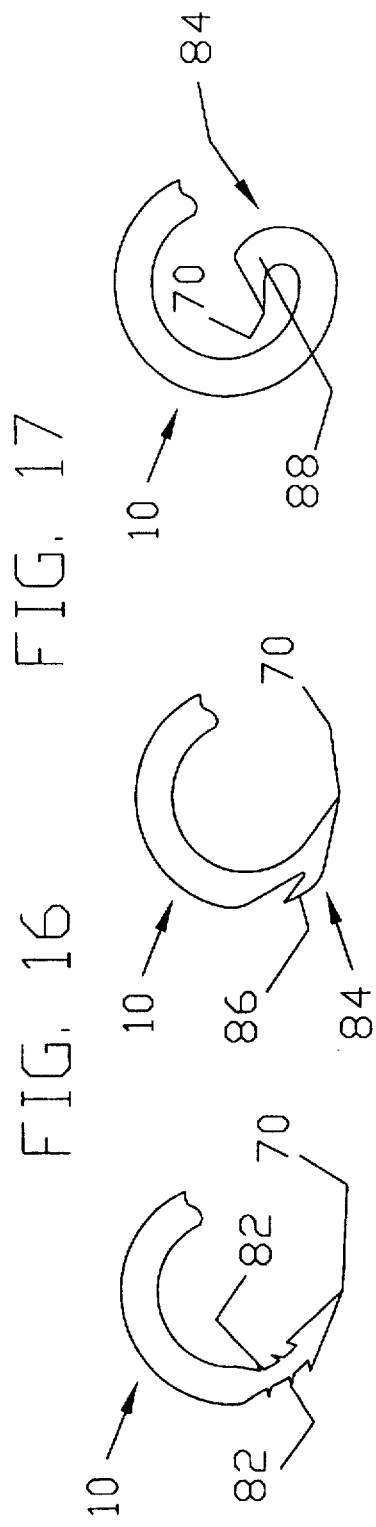

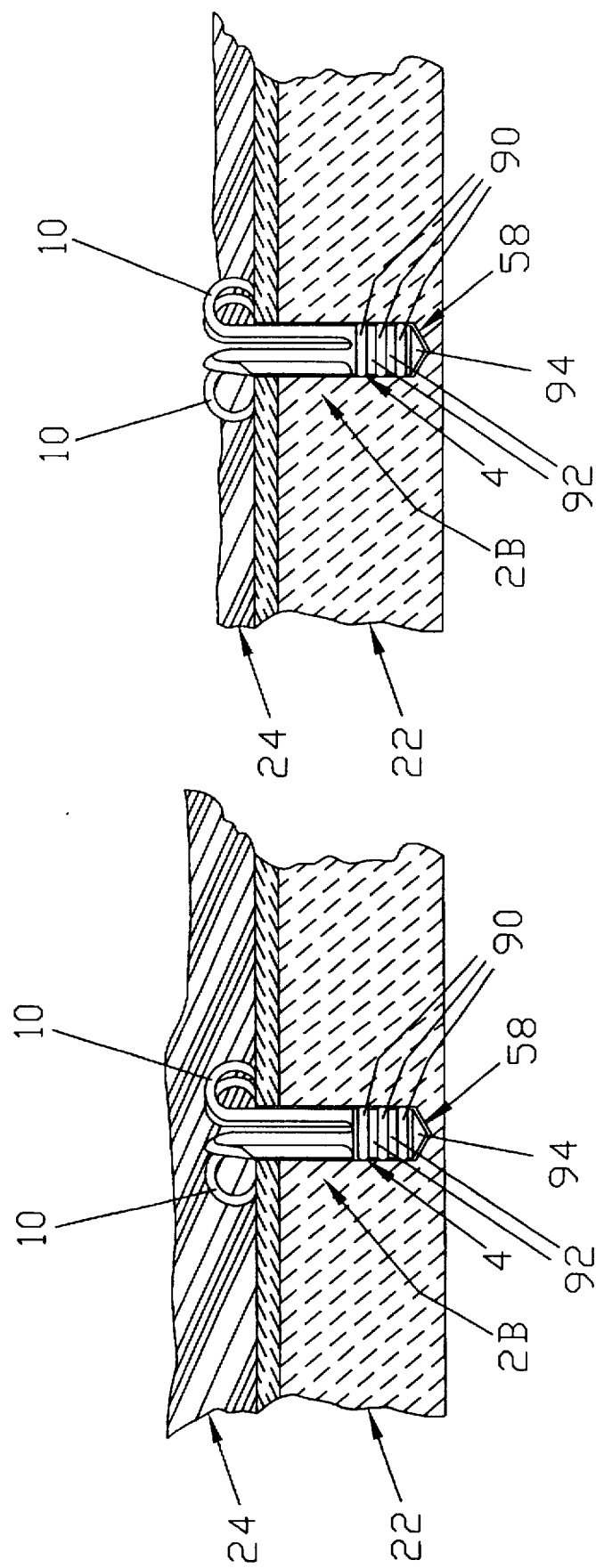

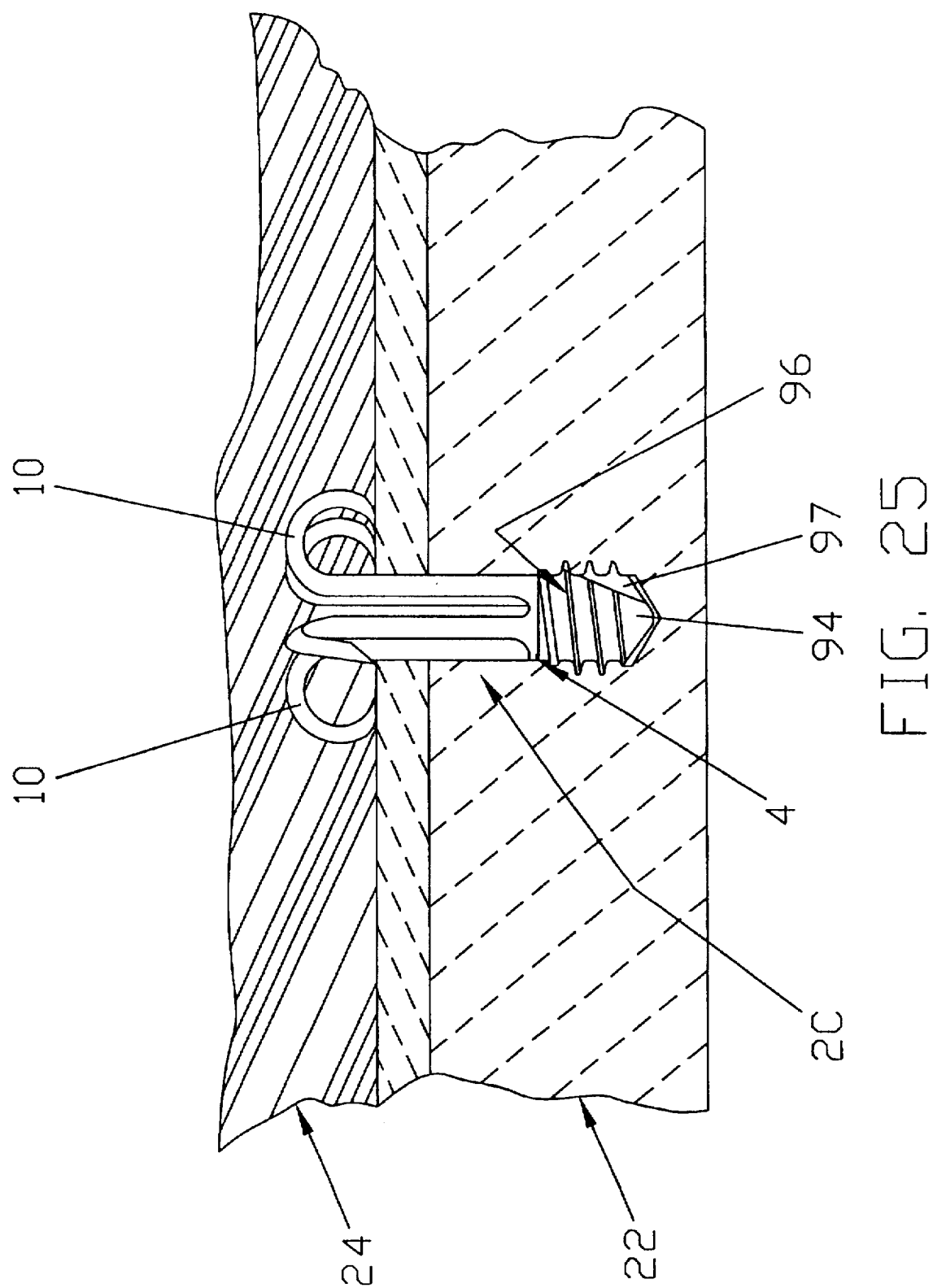

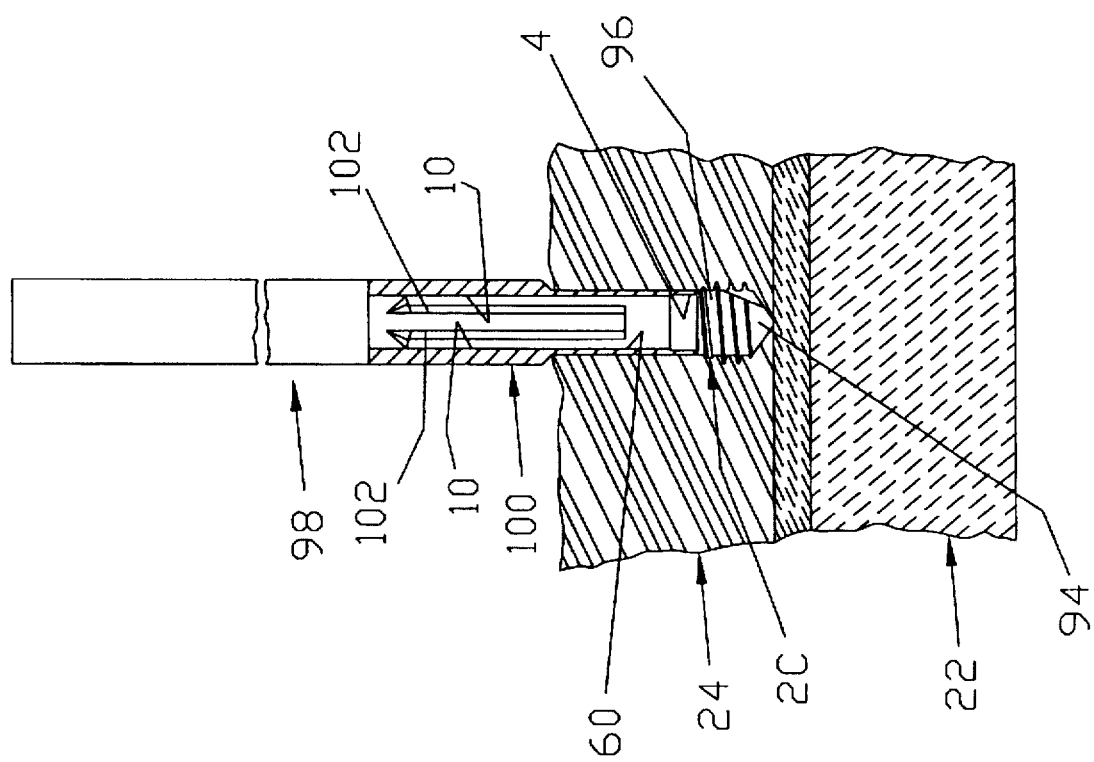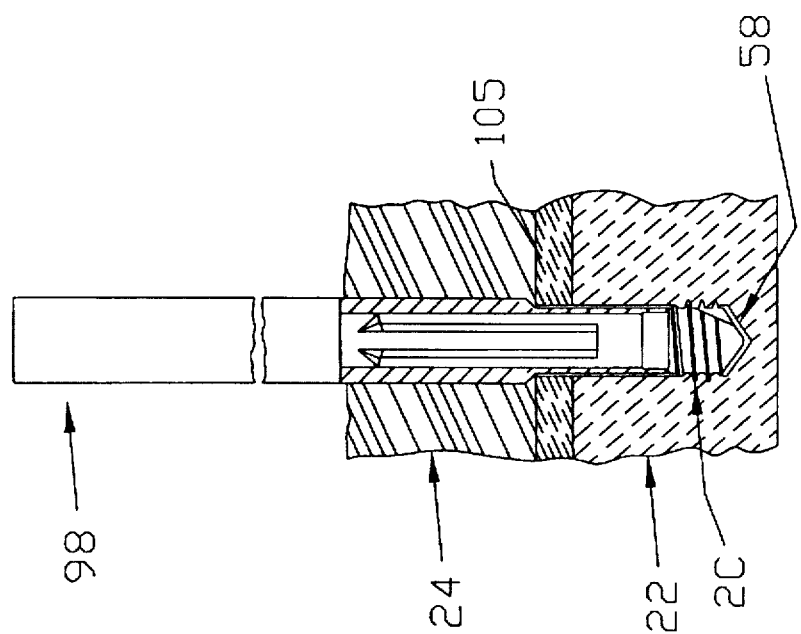

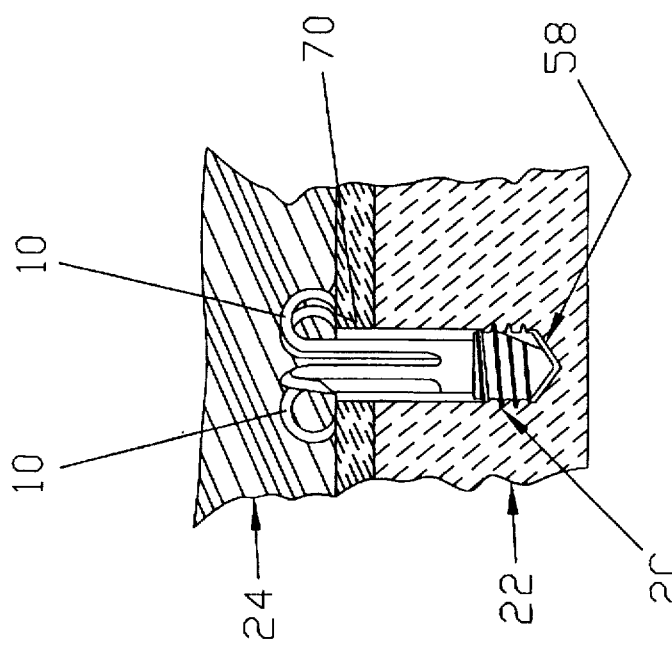
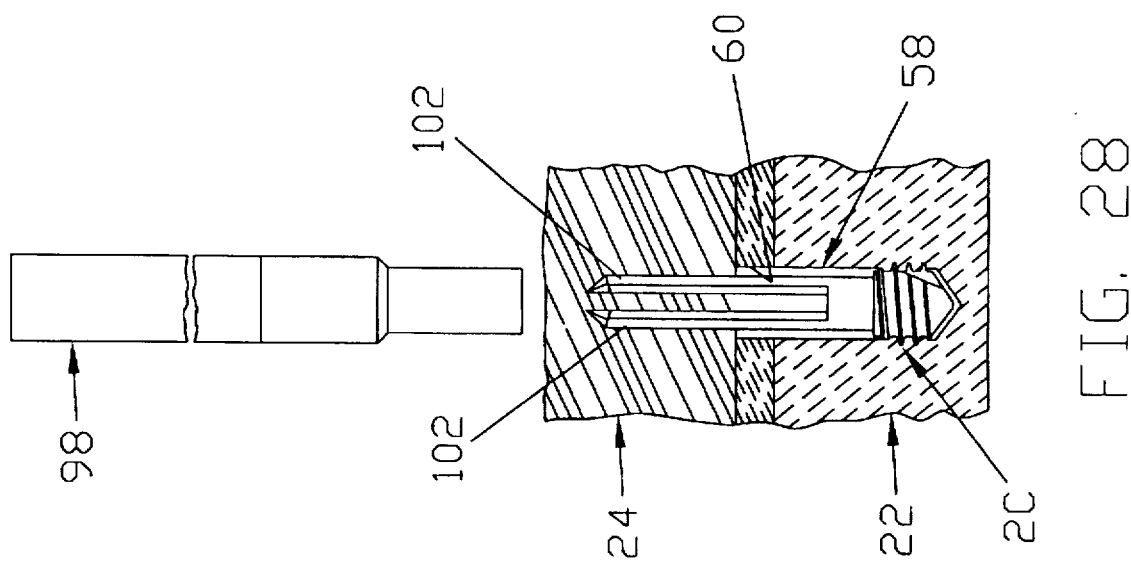

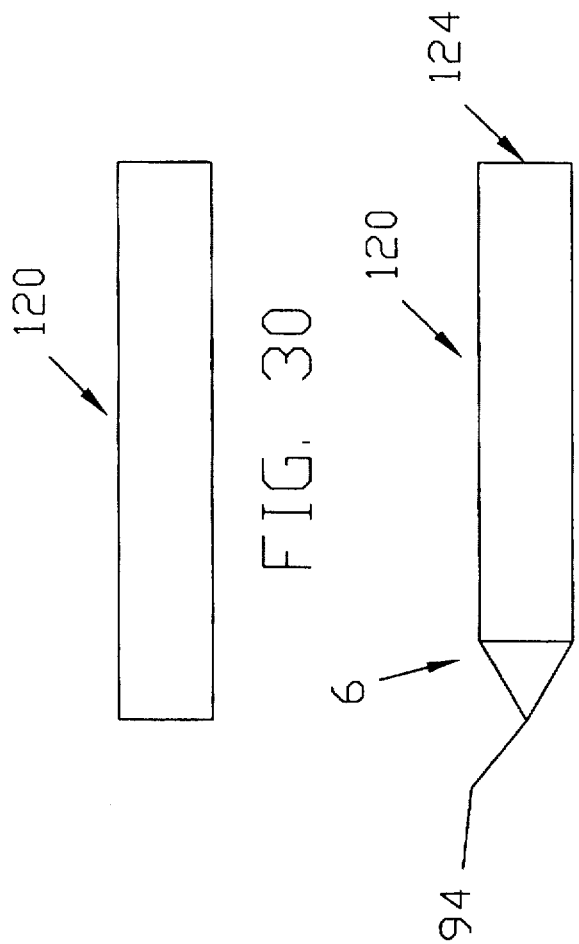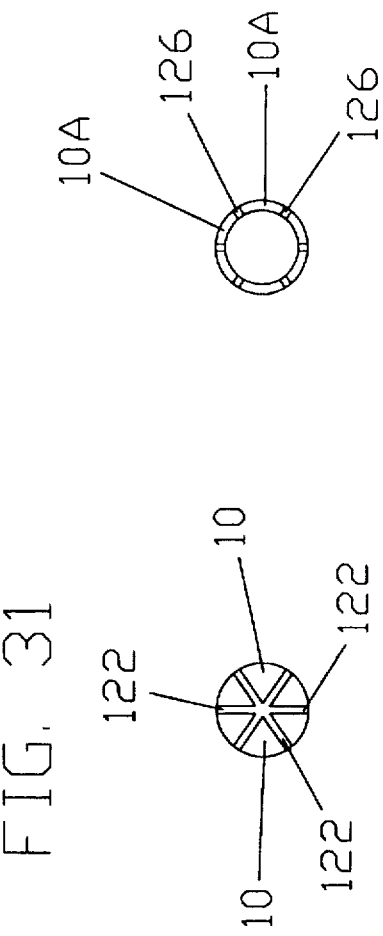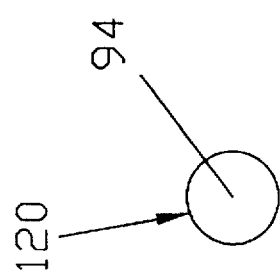

APPARATUS AND METHOD FOR BINDING A FIRST LAYER OF MATERIAL TO A SECOND LAYER OF MATERIAL

FIELD OF THE INVENTION

This invention relates to fasteners, methods, and tools for binding a first layer of material to a second layer of material, including the binding of soft tissue to bone.

BACKGROUND OF THE INVENTION

In the attachment of soft tissue, or the like, to bone, it has been customary to utilize suture anchors of the sort comprising (i) a body having bone engaging means, and (ii) a length of suture secured to the body, such that when the suture anchor is driven into the bone, the suture material can be used to tie the soft tissue to the bone. Such suturing generally requires skill, suturing tools, and room in which to maneuver. It also requires attention, on the part of the surgeon, to the possible knotting and/or entangling of suture strands during the procedure.

Thus, there is a need for tissue anchors, or fasteners, which operate to hold tissue on bone without the need for suture or other tie-down type fastening means.

More particularly, there is a need for a new type of tissue anchor, or fastener, which can be used to bind soft tissue to bone, and which may be manufactured simply and inexpensively, so as not to increase the overall cost of the fastening procedure.

There is also a need for a method for binding two layers of material together, such as tissue and bone, which method does not require suturing one layer to another.

In addition, there is a need for a simple, inexpensive and reliable tool for deploying the aforesaid fastener effectively and quickly.

OBJECTS OF THE INVENTION

It is, therefore, an object of the present invention to provide fasteners for binding one layer of material to another, including binding a layer of mammalian soft tissue to a layer of mammalian bone.

Another object of the invention is to provide a method for manufacturing such fasteners.

A further object of the invention is to provide an improved method for binding together two such layers of material.

A still further object of the invention is to provide appropriate tools for deploying the aforesaid fasteners so as to bind together the two layers of material.

SUMMARY OF THE INVENTION

These and other objects of the present invention are addressed by the provision and use of a novel fastener for binding a first layer of material to a second layer of material. The fastener comprises a body portion for disposition in a bore in the first layer, the body portion having means thereon for resisting movement of the body portion from the bore. The fastener further comprises gripper portions extending from the body portion and extendible through the second layer toward the first layer so as to bind the second layer to the first layer.

The objects of the present invention are further addressed by the provision and use of a novel fastener for binding a layer of mammalian soft tissue to a mammalian bone, the fastener comprising a body portion for disposition in a bore in the bone, with the body portion having means thereon for resisting movement of the body portion from the bore. The fastener further comprises gripper portions extending from the body portion and extendible through the layer of tissue toward the bone so as to bind the tissue to the bone.

The objects of the present invention are still further addressed by the provision and use of an alternative fastener for joining together first and second layers of material, the fastener comprising a body portion for disposition in a bore extending through the first and second layers. The fastener further comprises legs extending from an end of the body portion and, through confinement, conformable to a cross-section of the body portion, the legs being self-biased to extend radially outwardly from the body portion and, thereafter, in a direction generally parallel to a lengthwise axis of the body portion, upon removal of the confinement.

The objects of the present invention are still further addressed by the provision and use of a method for making a fastener for binding a layer of mammalian soft tissue to a mammalian bone, the method comprising the steps of providing a cylindrically-shaped member of a rigid material, and dividing a proximal portion of the member into a plurality of elongated legs and imbuing the legs with a self-bias toward curling outwardly and distally, and providing means on an undivided distal portion of the member for retaining the distal portion of the member in the bone.

The objects of the present invention are still further addressed by the provision and use of a novel method for binding to a first layer of material a second layer of material, the method comprising the steps of providing a bore in the first layer, overlaying the first layer with a second layer, and piercing the second layer with a cannula to provide an opening aligned with the bore. The method further comprises moving a fastener through the cannula and into the bore, and exposing means on a body portion of the fastener for engaging wall portions of the bore so as to retain the fastener in the bore, and withdrawing the cannula from the fastener so as to release legs extending from the body portion of the fastener, wherein the legs are self-biased to extend radially outwardly from the body portion and towards the first layer through the second layer so as to bind the second layer to the first layer.

The objects of the present invention are still further addressed by the provision and use of a tool for setting a fastener to bind together a first layer of material overlaid by a second layer of material, the first layer having a bore therein transverse to a surface thereof on which the second layer is disposed, and the fastener comprising a body portion having means thereon for locking the body portion in the bore, and legs extending from the body portion and self-biased to extend radially outwardly from the body portion, through the second layer, and distally through the second layer towards the first layer. The tool comprises a housing, a cannula and a plunger. More particularly, the housing comprises a tubular stem and, at one end thereof, an enlarged housing portion defining a chamber. The cannula is disposed in the stem, and includes a collar extending outwardly from a proximal end thereof. The distal end of the cannula has a penetration point. The collar is disposed in the chamber and is adapted to be adjacent to a distal wall of the enlarged housing portion. The plunger comprises a rod portion that is at least in part disposed in the cannula and in part adapted to be disposed in the chamber. The plunger further comprises a flange portion extending outwardly from the rod portion in the chamber and which is adapted to be disposed adjacent to a proximal wall of the housing, and a handle portion which is fixed to a proximal end of the rod and extending through an opening in the housing. The cannula is adapted to receive and retain the fastener, with the fastener body portion disposed proximate to the distal end of the cannula and the fastener legs extending proximally in the cannula. The tool is movable axially and distally so as to move the cannula penetration point through the second layer into alignment with the bore. The plunger is movable axially and distally to engage the fastener and to move the fastener into the bore and to move the flange portion into contact with the cannula collar in the chamber. The plunger flange portion has locking means thereon for interlocking the plunger flange portion and the cannula collar. The plunger is movable proximally in the housing to draw the locking means, and thereby the cannula, proximally so as to leave the fastener body portion disposed in the bore and to withdraw the cannula from the bore and from the second layer so as to release the fastener legs for the aforementioned self-biased movement outwardly and distally through the second layer.

The objects of the present invention are still further addressed by the provision and use of, in combination, a fastener for binding a first layer of material to a second layer of material, and a fastener-setting tool. The fastener comprises a body portion for disposition in a bore in the first layer, the body portion having means thereon for resisting movement of the body portion from the bore, and gripper portions extending from the body portion and extendible through the second layer toward the first layer so as to bind the second layer to the first layer. The tool comprises a cannula for making an opening in the second layer and holding therein the fastener, plunger means for pushing the fastener out of the cannula and into the bore, and means for withdrawing the cannula and the plunger means from contact with the fastener so as to permit the extension of the fastener's gripper portions through the second layer toward the first layer.

The objects of the present invention are still further addressed by the provision and use of, in combination, a fastener for binding a first layer of material to a second layer of material, and a fastener-setting tool. The fastener comprises a body portion for disposition in a bore in the first layer, the body portion having a pointed distal end and screw threads extending proximally therefrom, and gripper portions extending from the body portion and self-biased to extend outwardly and distally. The tool comprises a rod having a tubular portion at a distal end thereof for receiving, and releasably retaining, portions of the gripper portions therein. The rod is rotatable so as to threadedly drive the fastener through the second layer and the first layer to generate the bore and place the body portion of the fastener in the bore in the first layer, with the gripper portions extending proximally into the second layer and confined by the rod tubular portion. The rod is withdrawable from the gripper portions so as to permit the gripper portions to move in accordance with their self-bias outwardly and distally through the second layer towards the first layer. The fastener's screw threads resist movement of the fastener from the bore, and the gripper portions bind the second layer to the first layer.

The objects of the present invention are still further addressed by the provision and use of an alternative method for binding to a first layer of material a second layer of material, the method comprising the steps of providing a fastener having a body portion with a pointed distal end and screw threads extending proximally therefrom, the fastener further having legs extending proximally from the body portion, the legs being self-biased to extend outwardly and distally, but conformable under confinement to a cross-sectional area of the body portion throughout the extent of the legs, and providing a rotatable rod having a tubular distal end portion adapted to receive and retain proximal portions of the legs, with the distal end of the body portion being unconfined by the rod tubular portion. The method still further includes placing the proximal portions of the fastener's legs in the tubular portion, and overlaying the first layer of material with the second layer of material. The method further includes rotating the rod to threadedly drive the fastener body portion through the second layer and into the first layer, with the proximal portions of the fastener's legs being confined by the rod tubular portion, and withdrawing the rod from the fastener so as to enable the fastener legs to respond to their self-bias to extend outwardly and distally through the second layer to bind the second layer to the first layer.

BRIEF DESCRIPTION OF THE DRAWINGS

These and other features, objects and advantages of the present invention will be more fully disclosed or rendered obvious by the following detailed description of the preferred embodiments of the invention, which are to be considered in light of the accompanying drawings in which like reference numerals are used to designate like elements throughout, and further in which:

FIG. 10 is a side elevational view of the fastener of FIG. 1, shown deployed in layers of materials, the latter being shown in section;

FIG. 11 is similar to FIG. 10, but shows the fastener binding a relatively thin layer of material to an underlying layer of material;

FIG. 12 is a side elevational view of a portion of a gripper portion of a fastener;

FIG. 13 is an end view of the free end of the gripper portion of FIG. 12;

FIG. 14 is similar to FIG. 12, but shows a gripper portion of an alternative cross-sectional configuration;

FIG. 15 is a sectional view, taken along line 15—15 of FIG. 14;

FIGS. 16–20 are side elevational views of alternative embodiments of gripper portions of a fastener;

FIG. 23 is similar to FIG. 21, but shows still another alternative embodiment of fastener;

FIG. 24 is similar to FIG. 23, but shows the fastener of FIG. 23 binding a relatively thin layer to an underlying layer;

FIG. 25 is similar to FIG. 23, but shows another alternative embodiment of fastener;

FIGS. 26–29 are similar to FIGS. 2–9, but illustrate the use of an alternative tool and method for deployment of the fastener of FIG. 25;

FIGS. 30–34 illustrate method steps in the manufacture of one form of fastener; and FIG. 35 is similar to FIG. 33, but shows an alternative form of fastener.

DETAILED DESCRIPTION OF THE PREFERRED EMBODIMENTS

It is to be understood at the outset that the surgical context of use of the present invention which appears in the following description has been selected for convenience of illustration only. Certain features and advantages of the invention are particularly beneficial in this context, and certain modifications of the invention in its broader aspects have been developed with specific reference to its surgical utility. No limitation of the invention in its broader aspects is intended by the choice of this context for the following description, and none should be implied therefrom. Similarly, no limitation of the present invention is intended from the choice of descriptive terms for any of the elements discussed below, and none should be implied therefrom.

Figure 1:
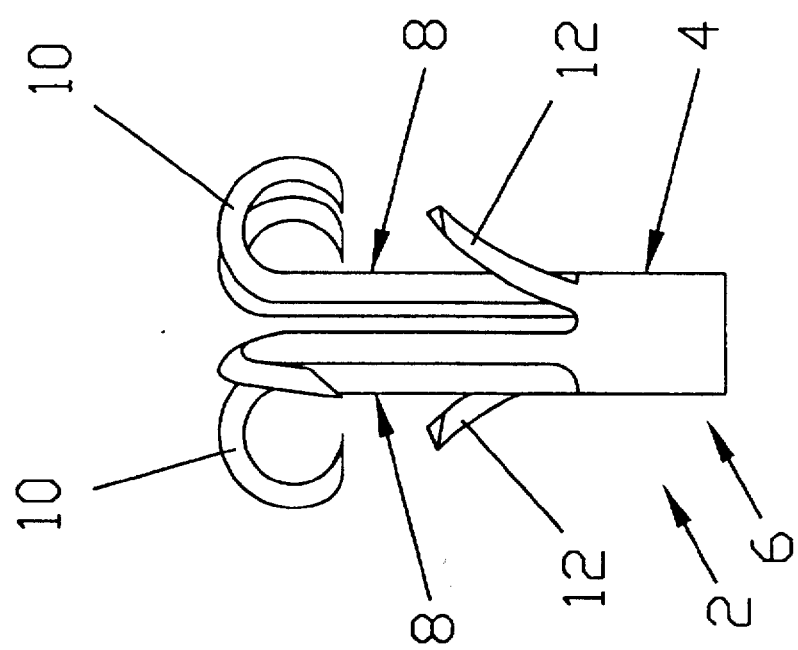
FIG. 1 is a side elevational view of one form of fastener illustrative of an embodiment of the invention.

Referring now to the drawings, and particularly to FIG. 1, there is shown an illustrative fastener 2 for binding together two bodies, or layers, of material. The fastener 2 includes a body portion 4 at a distal end 6 thereof, and gripper portions 8 extending proximally from body portion 4. The gripper portions 8 comprise a plurality of legs 10 which are self-biased, as by heat treatment, and/or by metallurgical composition, and/or by plastics or composite molding, or the like, to extend radially outwardly and distally, as shown in FIG. 1. A selected number of gripper portions 8, in manufacture, may be shortened, as by cutting, to provide barbs 12 self-biased to extend outwardly from body portion 4. The body portion 4 of fastener 2 is of a rigid, preferably solid, material, such as metal or dense rigid plastic, or a composite thereof, compatible with the material of the underlying layer. The legs 10 preferably are integral with body portion 4 and comprise the same material. One preferred material for the fastener is a so-called "shape memory alloy (SMA)/stress induced martensite (SIM)" material, such as a nickel-titanium alloy known as "Nitinol". See, for example, the SMA/SIM material disclosed in U.S. Pat. No. 4,665,906 issued May 19, 1987 to Jervis for MEDICAL DEVICES INCORPORATING SIM ALLOY ELEMENTS, which patent is specifically incorporated herein by reference.

Figure 2:
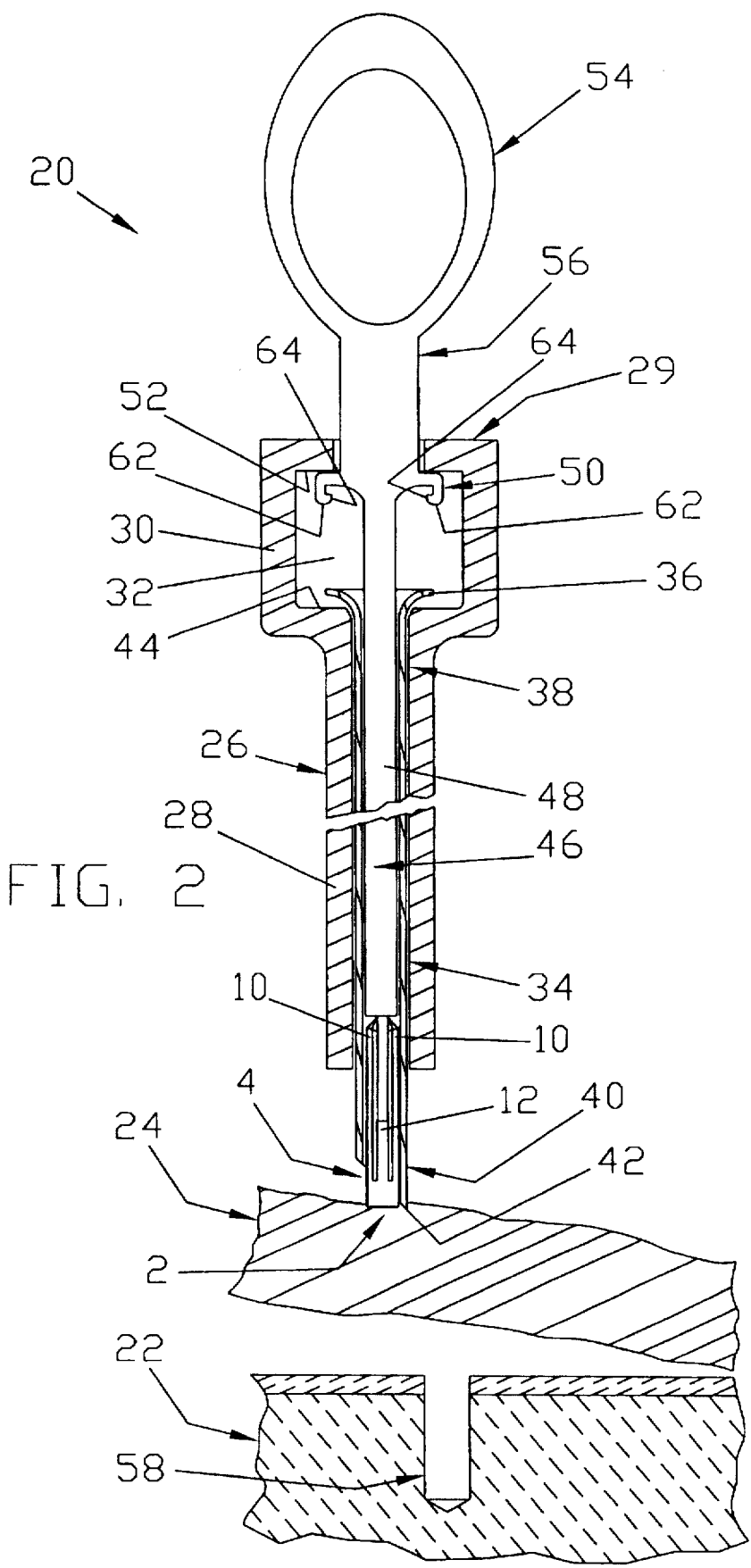
FIGS. 2–9 are partly sectional, partly elevational views illustrative of method steps for use of the inventive fastener of FIG. 1 and illustrative of a tool for use with the inventive fastener.
Figure 3:
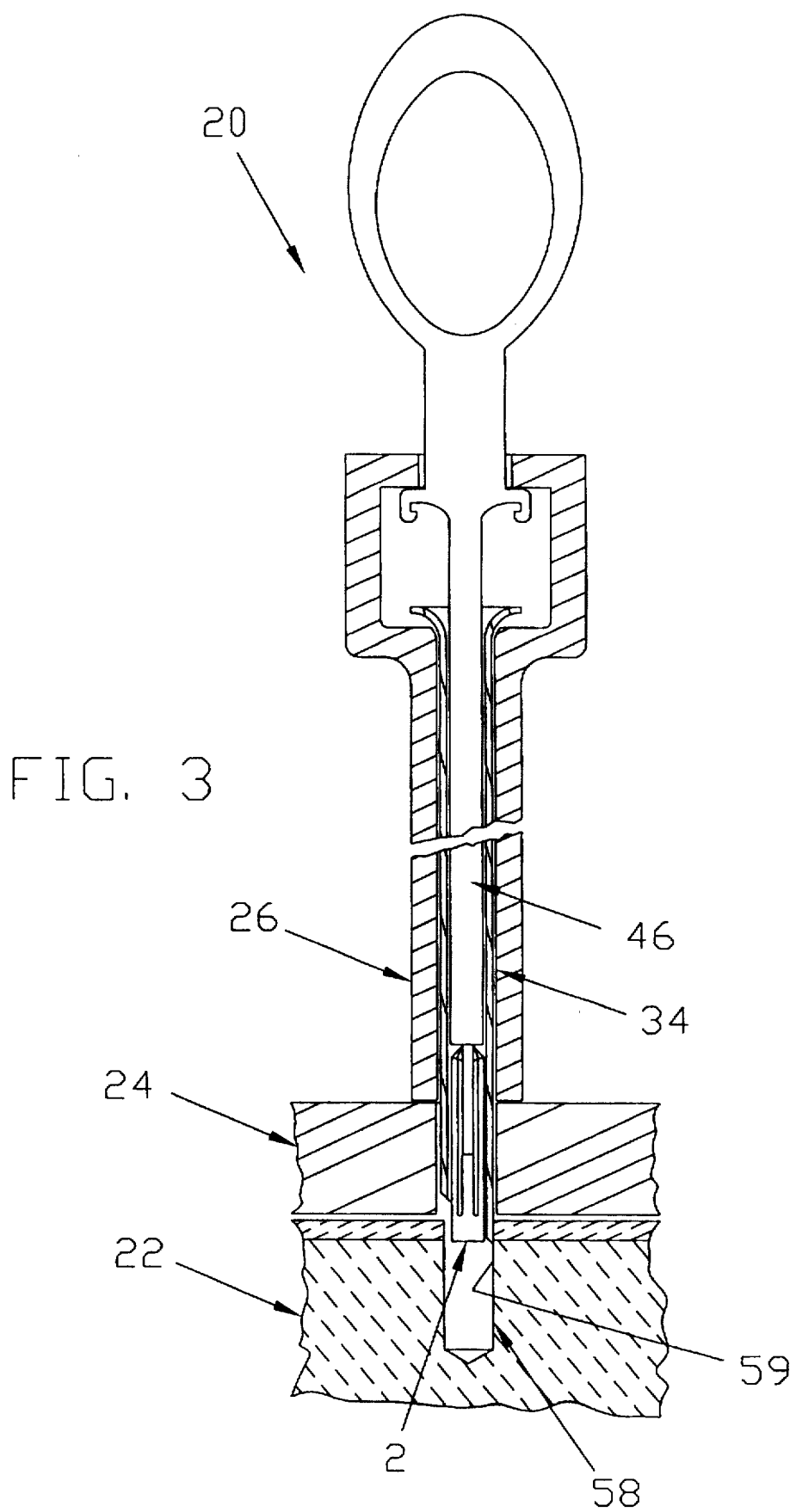
Figure 4:
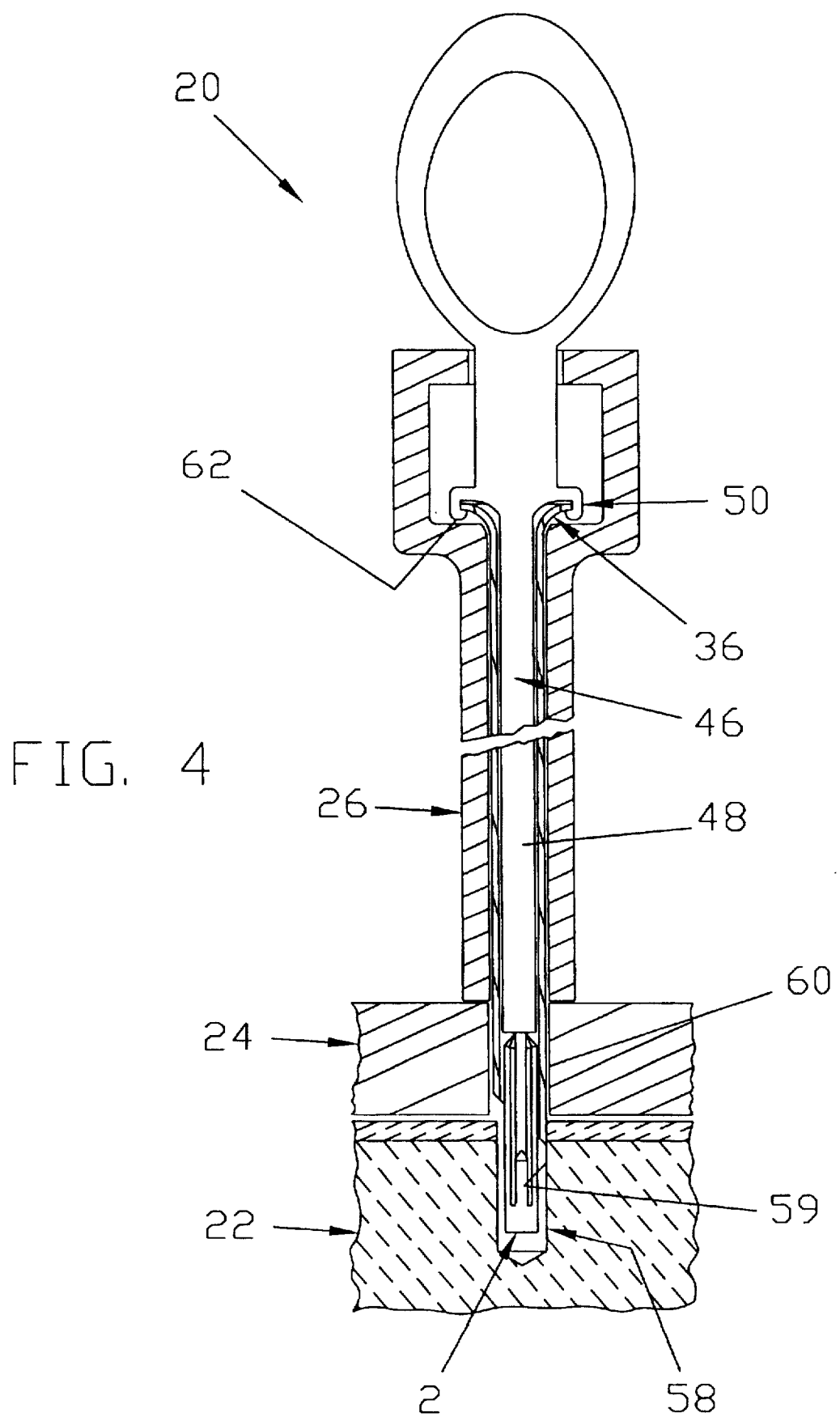
Figure 5:
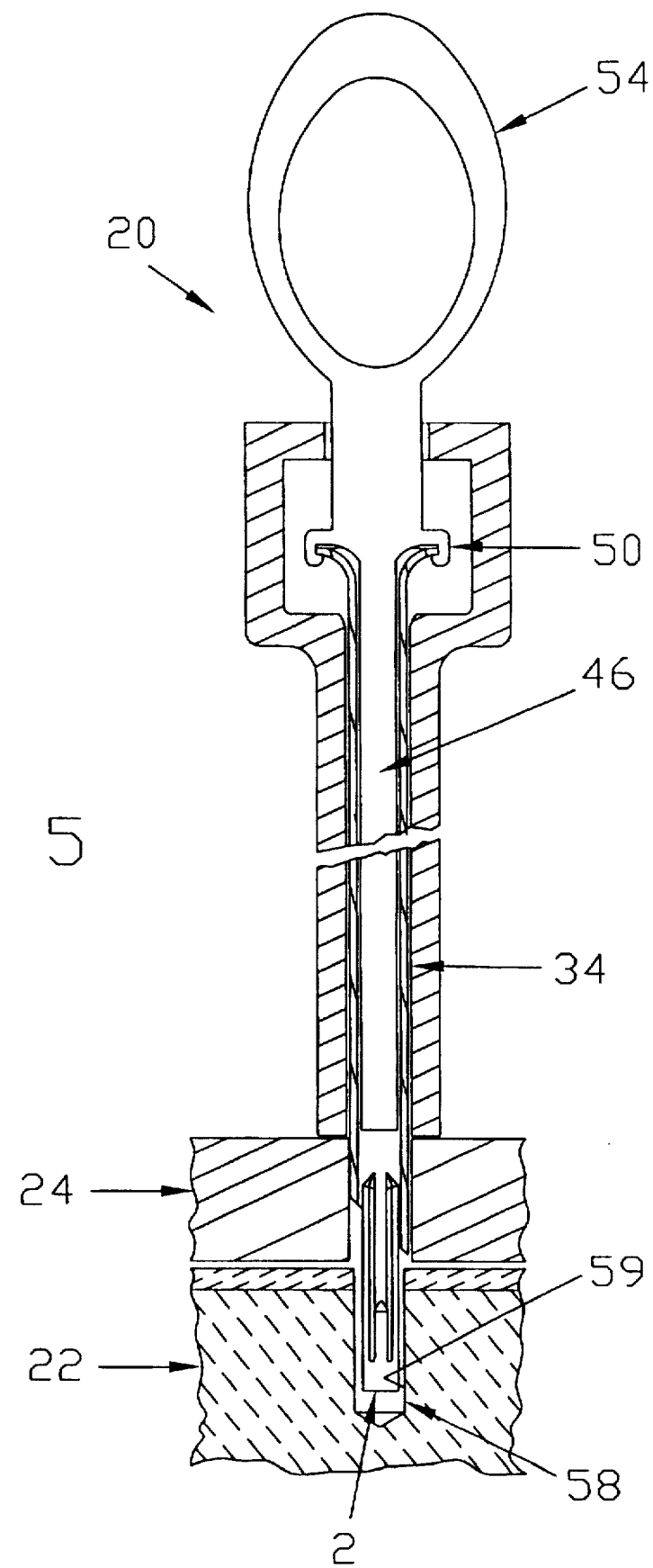

In FIGS. 2–9, there is shown a tool 20 for setting fastener 2 so as to bind together a first layer 22 of material and an overlying second layer 24 of material. The tool 20 includes a housing portion 26 having a tubular stem 28 and, at a proximal end 29 thereof, an enlarged housing portion 30 defining a chamber 32. A cannula 34 is disposed in stem 28 and is provided with a collar 36 extending radially outwardly from a proximal end 38 of cannula 34. Cannula 34 is provided with a distal end 40 having a penetration point 42. Collar 36 is disposed in chamber 32 and is adapted to be adjacent to a distal wall 44 of enlarged housing portion 30, as shown in FIGS. 2–4.

A plunger 46 is provided with a rod portion 48 disposed in cannula 34 and adapted to be disposed in part in chamber 32, as shown in FIGS. 2, 3 and 5–9. The plunger 46 is further provided with a flange portion 50 disposed in chamber 32 and adapted to be disposed adjacent to a proximal wall 52 of enlarged housing portion 30, as shown in FIGS. 2, 3 and 6–9. The plunger 46 is still further provided with a handle portion 54 fixed to a proximal end 56 of rod portion 48.

As shown in FIG. 2, cannula 34 is adapted to receive and retain fastener 2, with fastener body portion 4 disposed proximate distal end 40 of cannula 34 and fastener legs 10 extending proximally in cannula 34. When fastener 2 is disposed within cannula 34, legs 10 and any barbs 12 of fastener 2 are confined by cannula 34.

Before applying tool 20, first layer 22 is provided with a bore 58 and second layer 24 is laid over first layer 22 (FIG. 2). The tool 20 is then brought to bear against layer 24 and moved axially and distally so as to urge the cannula's penetration point 42 through second layer 24 and into alignment with bore 58 (FIG. 3). Plunger 46 is then moved axially and distally within housing portion 26 (FIG. 4) so as to engage fastener 2 (if the plunger's rod portion 48 is not already engaged with fastener 2) and to drive fastener 2 through an opening 60 (created by the piercing action of the cannula's distal end 40) and into bore 58. As soon as barbs 12 clear the cannula's distal end 40, barbs 12 are free to spring outwardly to engage and push into wall portions 59 of bore 58. The particular configuration of barbs 12 permits further movement of the fastener's body portion 4 into bore 58, but resists movement of body portion 4 out of bore 58 (FIGS. 7–10). In due course, the plunger's flange portion 50 engages the cannula's collar 36. The plunger's flange portion 50 is provided with locking means 62 thereon which are adapted to interlock with cannula collar 36 (FIG. 4). As shown in FIGS. 2–9, locking means 62 may comprise leaf-spring hook means 64 (FIG. 2) which are adapted to snap over cannula collar 36.

Figure 6:
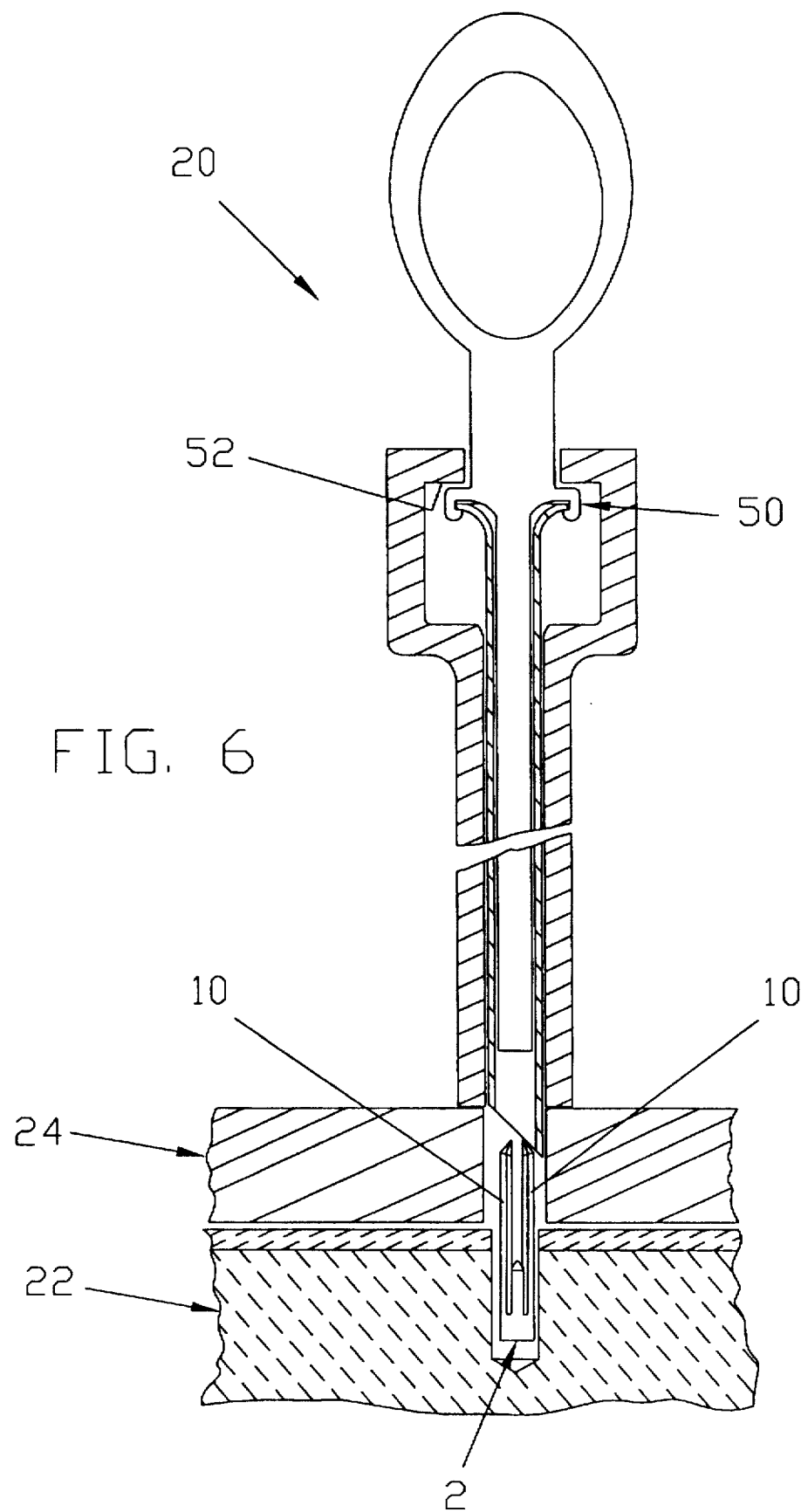
Figure 7:
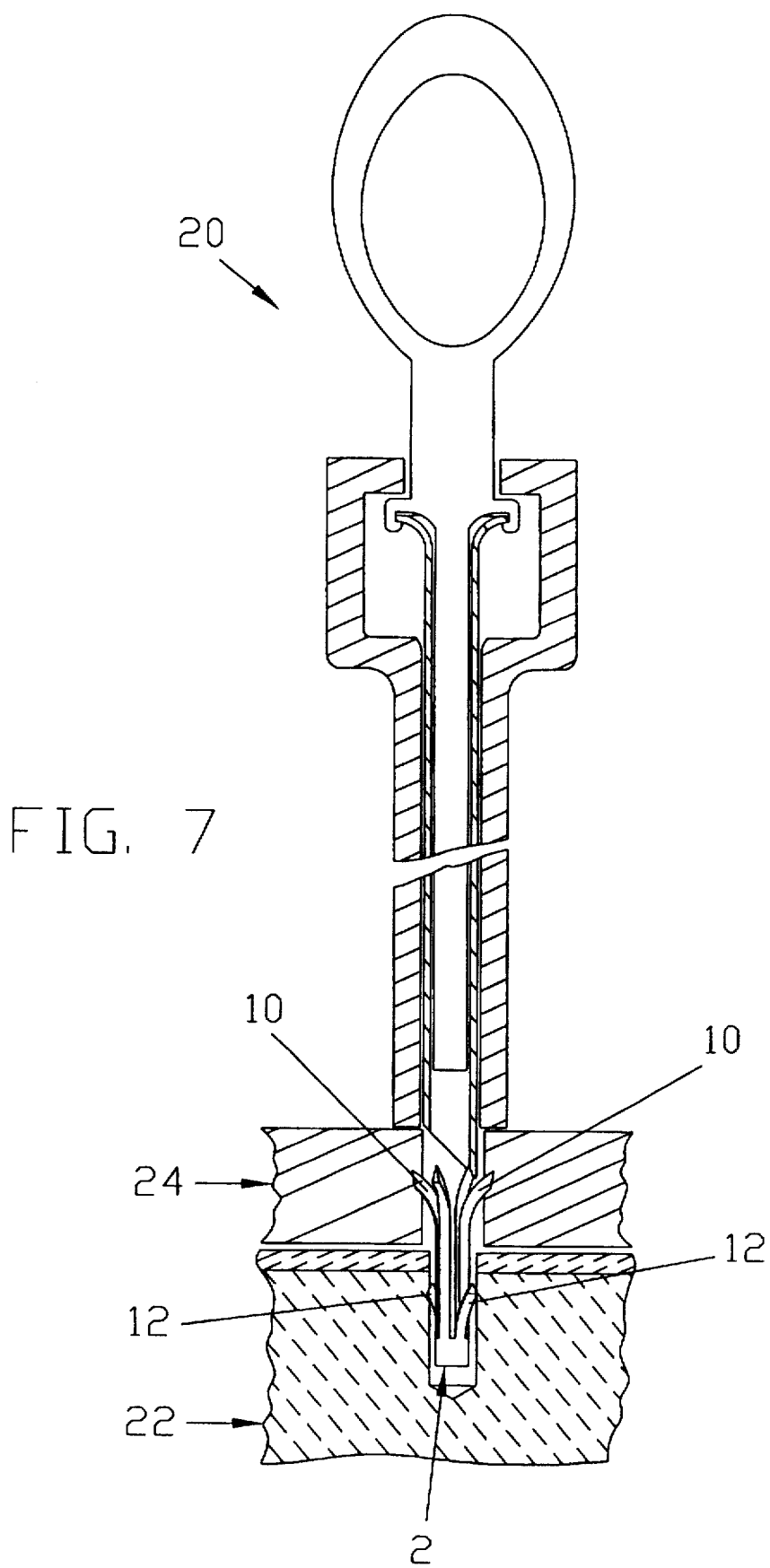
Figure 8:
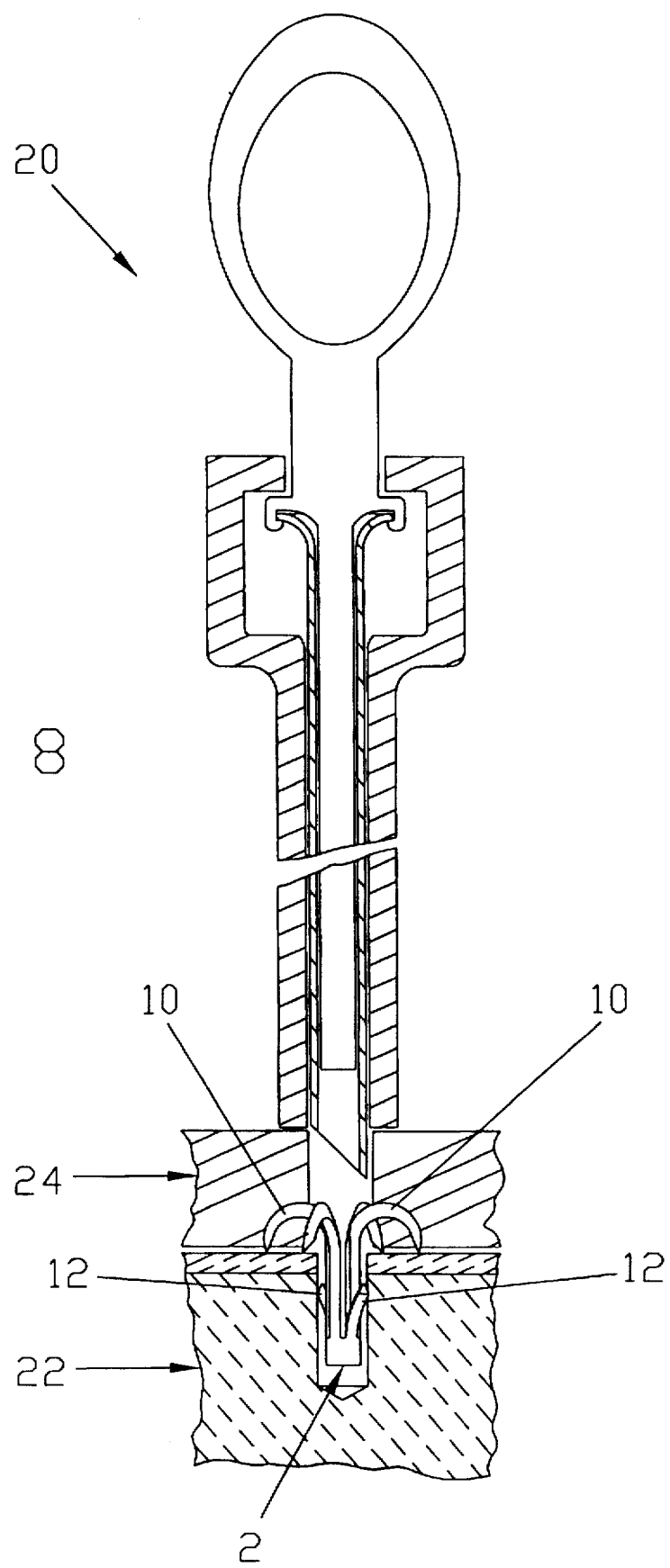
Figure 9:
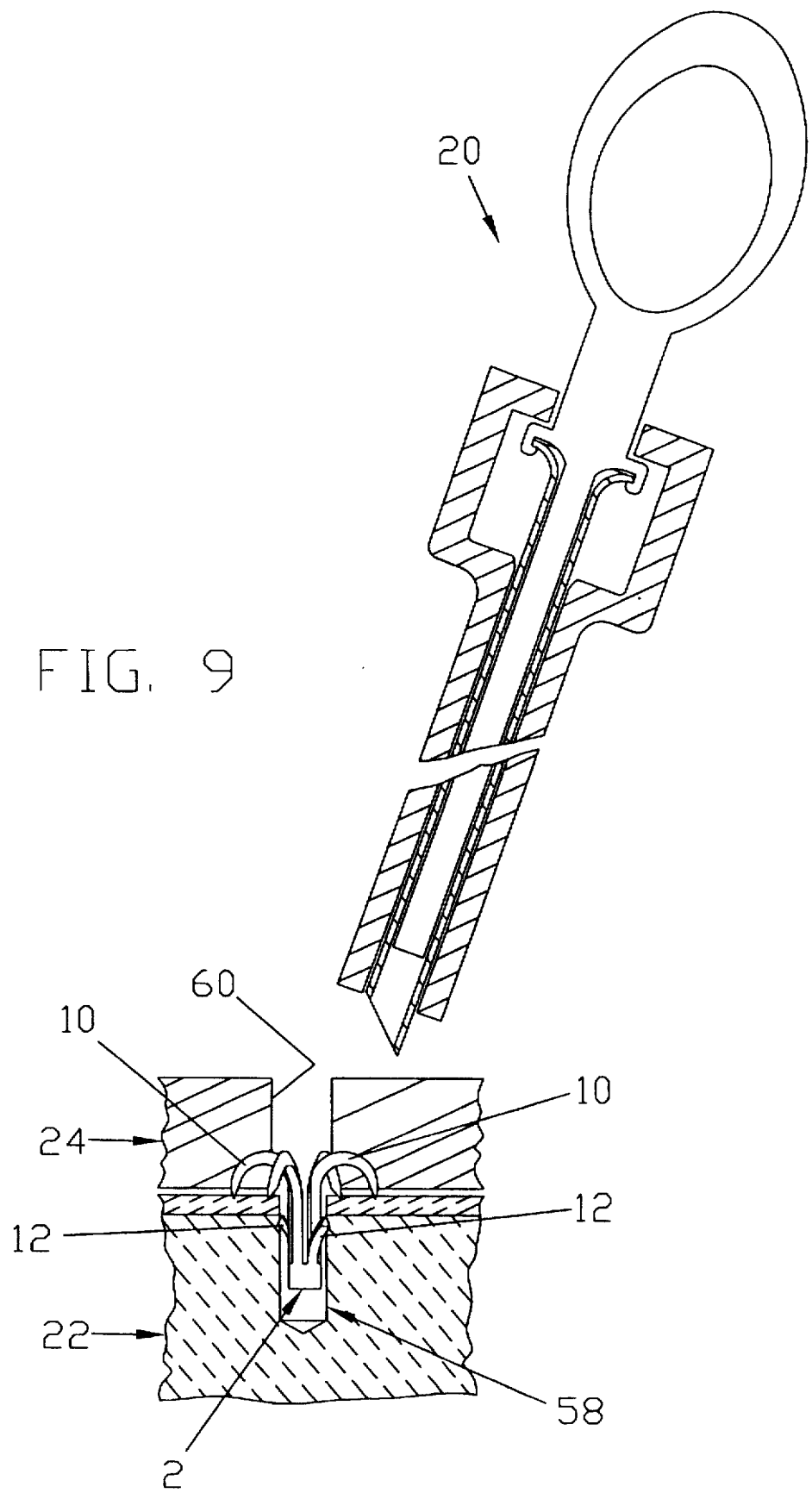

Upon proximal movement of handle portion 54 (FIG. 5), as by operator manipulation thereof, cannula 34 is drawn proximally, leaving fastener body portion 4 in bore 58 and, in due course, clearing the legs 10 of fastener 2 (FIG. 6). As a consequence, legs 10 are released from confinement, thereby permitting them to follow their self-bias so as to extend outwardly through second layer 24 (FIG. 7) and downwardly through layer 24 (FIG. 8) toward first layer 22. The proximal movement of plunger 46 in housing portion 26 causes the plunger's flange portion 50 to engage proximal wall 52 of housing enlarged portion 30 (FIGS. 6–8). Thereafter, tool 20 may be withdrawn from the fastener area (FIG. 9). As a result of the foregoing, fastener body portion 4 will be lodged in bore 58 (FIGS. 9 and 10), with barbs 12 resisting movement of body portion 4 from bore 58, and legs 10 being curled outwardly and downwardly (as viewed in FIGS. 8–10) so as to resist movement of second layer 24 from first layer 22. When second layer 24 is relatively soft mammalian tissue, the tissue substantially closes the opening 60 upon removal of cannula 34, thereby leaving fastener legs 10 embedded in, and covered by, tissue (FIG. 10). When first layer 22 is bone, barbs 12 typically bite into the cancellous bone region 22A. If fastener 2 should thereafter move upwardly, as viewed in FIG. 10, barbs 12 will engage the interior of the cortical bone region 22B which, being much harder than cancellous bone, will stop further movement of barbs 12 so as to prevent exiting of fastener 2.

While it is contemplated that it is beneficial that the legs 10 pass outwardly through second layer 24, it is recognized that in some instances the layer of tissue 24 will be relatively thin, as shown in FIG. 11. In such instances, legs 10 may have portions 66 standing proud of second layer 24, as shown in FIG. 11. Nevertheless, the plurality of legs 10 extending distally through layer 24 provides a binding mechanism which offers substantial resistance to movement of layer 24 from layer 22.

The legs 10 may comprise wire-like round strands, as shown in FIGS. 12 and 13. The legs 10 may comprise wires of shape-memory material, i.e., shape memory alloy (SMA)/stress induced martensite (SIM) material, fixed to fastener body portion 4. Alternatively, the legs 10 may be formed integrally with body portion 4, as noted above. In FIGS. 14 and 15, there is shown a leg 10 of triangular cross-section, which preferably is formed integrally with body portion 4, as will hereinafter be described in further detail.

The free ends of legs 10 preferably are provided with needle points 70, shown in FIGS. 12–20. In one embodiment (FIG. 12), the needle point 70 is simply a sharpened central point formed by a conical end portion 72 of the aforementioned wire-like round leg 10.

In FIG. 14, there is shown the aforementioned triangular cross-sectional leg 10. In this embodiment, the needle point 70 is formed by a convergence of three planar sides 74.

In FIGS. 16–20 there are shown various embodiments wherein legs 10 are provided with needle points 70 of alternative configurations and, in addition, with means for enhancing the gripping engagement between legs 10 and the second layer 24. In FIG. 16, an area 76 of leg 10 extending from needle point 70 is roughened. In FIG. 17, an area 78 near needle point 70 comprises a series of widthwise ribs 80 spaced from each other. In FIG. 18, the leg 10 is provided with barbs 82. In FIGS. 19 and 20, there are provided on the legs 10 hook means 84, the former (FIG. 19) including a reverse hook 86, and the latter (FIG. 20) having a "pig tail" hook 88.

It will be apparent that various features depicted in FIGS. 12–20 can be combined in any number of ways and that the particular features shown are merely illustrative of a wide range of leg configurations and gripping enhancement means.

Figure 21:
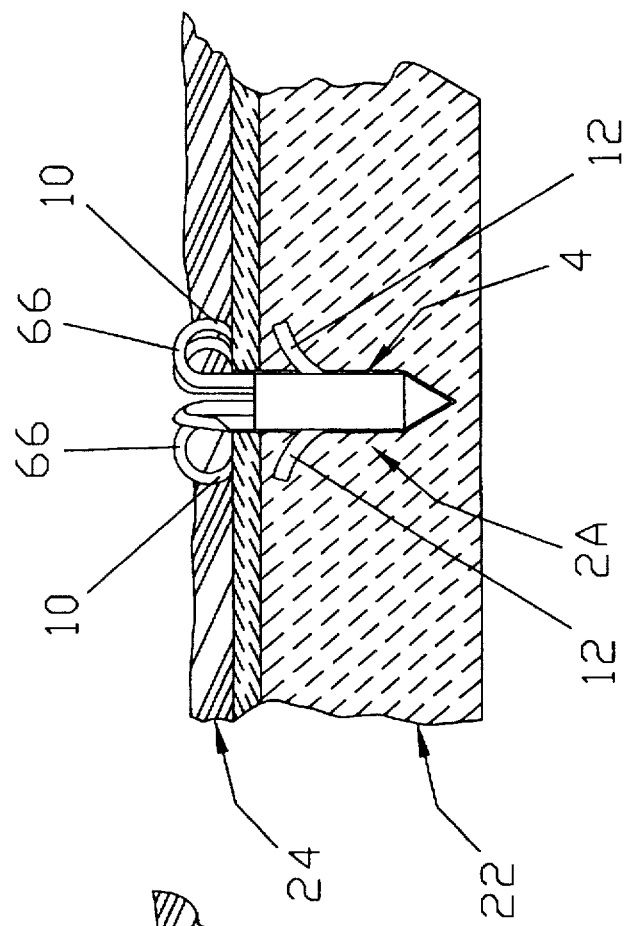
FIG. 21 is similar to FIG. 10 but shows an alternative embodiment of fastener.
Figure 22:
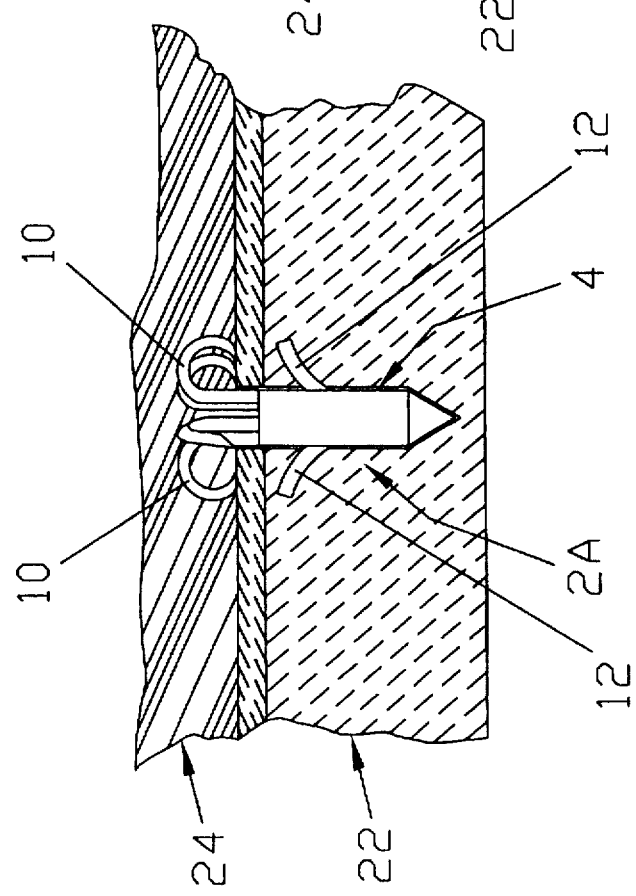
FIG. 22 is similar to FIG. 21, but shows the fastener of FIG. 21 deployed to bind a relatively thin layer to an underlying layer.
Figure 34:
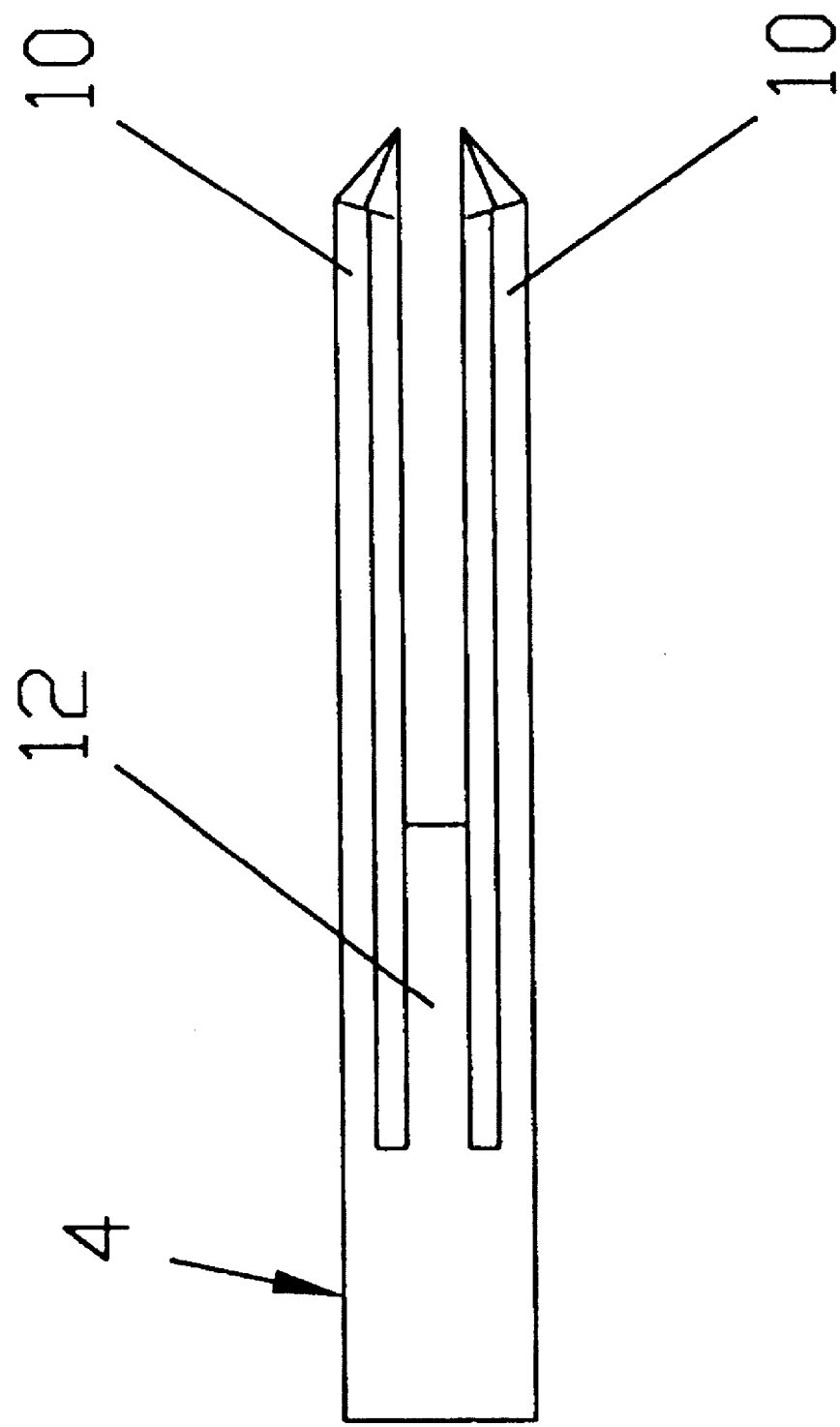

Referring to FIG. 21, it will be seen that in an alternative fastener embodiment 2A, the barbs 12 extend from the fastener body portion 4, but are disposed on body portion 4 distally of the legs 10. By way of example but not limitation, barbs 12 and fastener body portion 4 might have a geometry similar to the distal end of the suture anchor disclosed in U.S. Pat. No. 5,207,679, issued May 4, 1993 to Li for SUTURE ANCHOR AND INSTALLATION TOOL, which patent is specifically incorporated herein by reference. Again, if used to attach a thin second layer 24 (FIG. 22) to a first layer 22, the legs 10 may extend beyond the outer surface of the second layer, but will still exercise a substantial retaining force on the second layer.

In FIGS. 23 and 24, there is shown an alternative embodiment of fastener 2B wherein the fastener body portion 4 is provided with ribs 90 extending widthwise around the body portion 4 and spaced from each other. Ribs 90 define friction bands with grooves 92 therebetween. Ribs 90 and grooves 92 provide for an interference fit between fastener 2B and bore 58 and serve to resist movement of fastener 2B from bore 58.

If it is desired that fastener 2B be tapped through second layer 24 into first layer 22, the body portion 4 may be provided with a penetration point 94. Similarly, the embodiments of fasteners 2 and 2A illustrated in FIGS. 1 and 21 may also be provided with penetration points. It will be apparent that provision of the penetration point 94 may render the provision of bore 58 in first layer 22 unnecessary, or may provide a fastener guide means for use in conjunction with a bore previously provided.

In FIG. 25 there is shown an alternative embodiment of fastener 2C in which body portion 4 is provided with penetration point 94 and screw threads 96 extending proximally therefrom. One or more cutting flutes 97 may also be provided.

In use, the fastener 2C of FIG. 25 is inserted into a rotatable rod 98 (FIG. 26) having a tubular distal end portion 100 adapted to receive and retain proximal portions 102 of legs 10. Under confinement, legs 10 generally conform to the cross-sectional boundaries of fastener body portion 4, as shown in FIG. 26. The self-bias of legs 10 to extend outwardly provides for a friction fit between fastener 2C and rod 98. Threaded body portion 4 of fastener 2C is unconfined by tubular portion 100 of rod 98. Preferably the proximal body portion 4 is confined by, and is adapted to make a driving engagement with, tubular distal end portion 100, whereby rotatable rod 98 can impart a rotary motion to fastener 2C, yet can still release fastener 2C in an axial direction. In particular, the distal end of fastener 2C preferably has a configuration generally similar to the distal end of the suture anchor disclosed in U.S. patent application Ser. No. 08/393,553, filed Feb. 23, 1995 by Goble et al. for SUTURE ANCHOR ASSEMBLY (which patent application is hereby specifically incorporated herein by reference), including screw threads, cutting flute and a hex driving portion; and the distal end of rotatable rod 98 preferably includes a counterpart hex-shaped recess for making a driving engagement with fastener 2C.

In use, rod 98 is caused to rotate, as by a drill (not shown), to rotate fastener 2C such that the penetration point 94 and screw threads 96 cut opening 60 through second layer 24 and advance penetration point 94 to the surface of first layer 22 (FIG. 26). Continued rotation of rod 98 causes fastener body portion 4 to drill into first layer 22, the fastener thereby generating bore 58. After tubular distal end portion 100 (and fastener 2C) have penetrated a sufficient distance into first layer 22, e.g. after the tool's shoulder 105 engages the proximal surface of first layer 22 (FIG. 27), rod 98 is backed off leg proximal portions 102 (FIG. 28), which thereby become unconfined. Reacting to the aforementioned self-bias, legs 10 extend radially outwardly and distally, through second layer 24 and toward first layer 22. Upon completion of this movement (FIG. 29), needle points 70 of legs 10 are disposed proximate first layer 22. Depending upon the density and thickness of second layer 24 and the self-bias force with which legs 10 are imbued, needle points 70 may engage first layer 22, as shown in FIG. 29, or they may be adjacent thereto but spaced somewhat therefrom.

In FIGS. 30–35 there are illustrated steps in one preferred method for making fastener 2. The illustrative method includes providing a solid cylindrically-shaped dowel 120 (FIG. 30) of rigid material, as hereinabove described. If a penetration point 94 is desired on distal end 6, and/or body portion retaining means, such as those shown in FIG. 21 (barbs 12), and/or FIG. 23 (friction bands 90), and/or FIG. 25 (threads 96), such penetration point 94 (FIGS. 31 and 32) and retaining means are added, or machined into, the dowel 120 (the latter not being shown in FIG. 31, but being shown in FIGS. 1, 21, 23 and 25). Legs 10 are then formed, as by cutting length-wise slots 122 (FIG. 33) from a proximal end 124 of dowel 120. Slots 122 define triangularly-shaped legs 10 (FIGS. 14, 15, 33 and 34) extending from body portion 4 of fastener 2.

Legs 10 are imbued with a self-bias to curling outwardly and distally of fastener body portion 4. As noted above, such self-bias is known and any appropriate method may be used to imbue legs 10 with a bias outwardly and distally of fastener 2.

If a body portion retaining means has not been added or machined into fastener body portion 4 by the time legs 10 have been formed, selected legs 10 may be shortened to provide barbs 12 (FIG. 34) which can serve as body portion retaining means (FIG. 10).

In an alternative method, the dowel 120 may be solid in the area where body portion 4 will be, and tubular in the area where gripper portion 8 will be. Slots 126 (FIG. 35) provided in the gripper portion 8 form legs 10A which, rather than being triangular in cross-section as shown in FIG. 33, are arc portions of an annular wall, as shown in FIG. 35. Alternatively, dowel 120 may be tubular along its entire length if desired.

Once the legs 10 are formed, the legs may be provided with needle points 70 and/or the rough textured area 76, friction bands 80, barbs 82, and hooks 84, shown in FIGS. 16–20, to enhance engagement between legs 10 and second layer 24. After the fastener is formed, if unconfined, it will assume the deployed configuration shown in FIG. 1.

In still another method for making the fastener, the body portion 4 and gripper portions 8 may be formed separately and the legs 10 subsequently joined to body portion 4. In this embodiment, the legs 10 may comprise Nitinol or other shape-memory alloy wires, joined to a body portion 4 made of a material which is compatible with the material of legs 10, e.g., a suitable metal or plastic material. In this embodiment, legs 10 may be provided with means for enhancement of engagement between the legs 10 and the second layer 24, such as those shown in FIGS. 16–20, before legs 10 are joined to body portion 4. Similarly, the retention means for retaining body portion 4 in first layer 22 preferably is added to body portion 4 before joining body portion 4 with gripper portion 8, unless the retention means comprises shortened ones of the gripper portion legs 10. In the latter case, legs 10 may be shortened either before or after juncture of legs 10 and body portion 4.

It is also anticipated that some or all of the fastener may be made out of a material which is absorbable by the body. Thus, for example, it is anticipated that the fastener could have a body portion formed out of a suitable absorbable material and its legs formed out of a SMA/SIM material, or the entire fastener could be formed out of a suitable absorbable material.

Thus, there are provided fasteners for binding one layer of material to another, including binding a layer of mammalian soft tissue to a layer of mammalian bone, and methods for binding together such layers of material. There are further provided methods for making such fasteners and tools for deploying such fasteners to bind together the layers of material.

It is to be understood that the present invention is by no means limited to the particular constructions and method steps herein disclosed and/or shown in the drawings, but also comprises any modifications or equivalents within the scope of the claims.

What is claimed is:

1. A tool for setting a fastener to bind together a first layer of material overlaid by a second layer of material, the first layer having a bore therein transverse to a surface thereof on which the second layer is disposed, and said fastener comprising a body portion having means thereon for locking said body portion in the bore, and legs extending from said body portion and self-biased to extend radially outwardly from said body portion, and distally through the second layer towards the first layer, said tool comprising:

a housing portion including a tubular stem and at one end thereof an enlarged housing portion defining a chamber;

a cannula disposed in said stem, said cannula having a collar extending outwardly from a proximal end thereof, and having at a distal end thereof a penetration point, said collar being disposed in said chamber and adapted to be adjacent a distal wall of said enlarged housing portion; and a plunger having a rod portion at least in part disposed in said cannula and in part adapted to be disposed in said chamber, a flange portion extending outwardly from said rod portion in said chamber and adapted to be disposed adjacent a proximal wall of said housing, and a handle portion fixed to a proximal end of said rod and extending through an opening in said housing;

said cannula being adapted to receive and retain said fastener with said fastener body portion disposed proximate said distal end of said cannula and said fastener legs extending proximally in said cannula;

said tool being movable axially and distally to move said cannula penetration point through the second layer into alignment with the bore;

said plunger being movable axially and distally to engage said fastener and to move said fastener into the bore and to move said flange into contact with said cannula collar in said chamber;

said plunger flange portion having locking means thereon for interlocking said plunger flange portion and said cannula collar upon said contact;

said plunger being movable proximally in said housing to draw said locking means and thereby said cannula proximally to leave said fastener body portion in the bore and withdraw said cannula from the bore and from the second layer to release said fastener legs for said self-biased movement outwardly and distally through the second layer.

2. A fastener for binding a first layer of material to a second layer of material overlying and covering the first layer of material, said fastener comprising:

a unitary undivided body portion for disposition in a bore in the first layer, said body portion having a cross-sectional configuration, a longitudinal axis, and means thereon for resisting movement of said body portion from the bore, said means comprising barbs having free ends which extend toward the second layer; and gripper portions comprising elongated wire-like legs extending from said body portion and having needle pointed free ends, said legs being (1) conformable through confinement to an axial projection of said cross-sectional configuration, and (2) self-biased for extension, upon removal of said confinement, radially outwardly from, and parallel to, said axial projection of said cross-sectional configuration, through said second layer, such that each said leg extends to a position in said second layer wherein its free end is disposed proximate said first layer to bind said second layer to said first layer.

* * * * *